United States Patent [19]

O'Rourke

[11] Patent Number: 4,813,949
[45] Date of Patent: Mar. 21, 1989

[54] DOG DIAPER

[76] Inventor: Julia A. O'Rourke, 1133 Creedmoor Ave., Pittsburgh, Pa. 15226

[21] Appl. No.: 927,923

[22] Filed: Nov. 6, 1986

[51] Int. Cl.[4] .................. A61F 13/16; A01K 23/00
[52] U.S. Cl. ............................. 604/391; 604/394; 119/95
[58] Field of Search .............. 604/327, 346, 347, 358, 604/378, 385, 386, 387, 389, 390–394; 54/78, 79; 119/95, 143; D24/50

[56] References Cited

U.S. PATENT DOCUMENTS

| 2,290,110 | 7/1942 | McGraw | 604/385.1 |
|---|---|---|---|
| 2,974,635 | 3/1961 | McDowell | 119/143 |
| 3,141,461 | 7/1964 | Farris | 604/391 |
| 3,211,132 | 10/1965 | Hersh | 54/79 |
| 4,095,562 | 6/1978 | Graham | 119/95 |
| 4,133,297 | 1/1979 | Denebeim | 119/143 |
| 4,475,912 | 10/1984 | Coates | 604/385 |
| 4,527,991 | 7/1985 | Msarsa | 604/399 |
| 4,568,342 | 2/1986 | Davis | 604/391 |
| 4,577,591 | 3/1986 | Wesseldine | 604/398 |

FOREIGN PATENT DOCUMENTS

| 577401 | 6/1924 | France | 119/143 |
|---|---|---|---|
| 683622 | 6/1930 | France | 119/143 |
| 54864 | 12/1950 | France | 604/385.1 |
| 1089021 | 3/1955 | France | 604/392 |
| 2544194 | 10/1984 | France | 604/358 |
| 2574286 | 6/1986 | France | 604/387 |

Primary Examiner—C. Fred Rosenbaum
Assistant Examiner—Sharon Rose
Attorney, Agent, or Firm—Webb, Burden, Ziesenheim & Webb

[57] ABSTRACT

A diaper for a dog or other small quadruped comprises a textile body band and tail band forming a T with fasteners at one or both ends of the body band and the end of the tail band and an absorbent pad affixed to the inside surface of the tail band at its junction with the body band. The body band is wrapped around the dog's body with its ends on its back and those ends are connected by their fasteners. The tail band is brought over its rump and back and fastened to the body band ends at their junction so that the absorbent pad is against the dog's genital and anal areas. The tail band may be unitary with an opening for the dog's tail, or bifurcated.

2 Claims, 2 Drawing Sheets

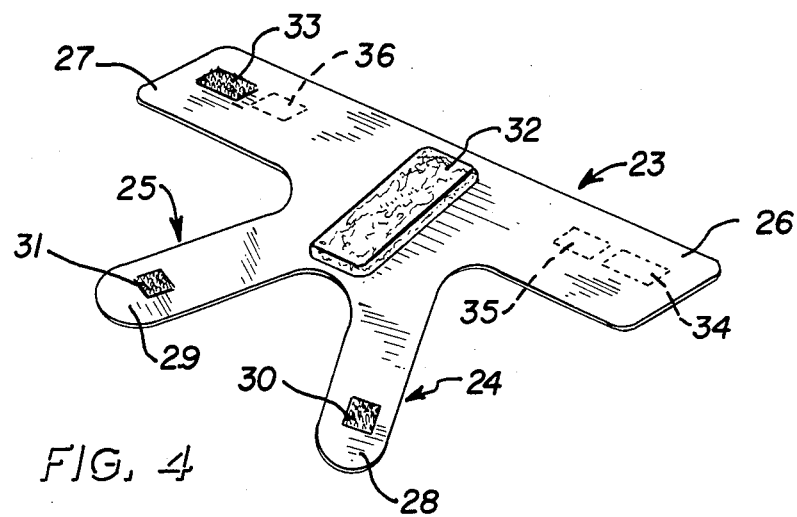
FIG. 4
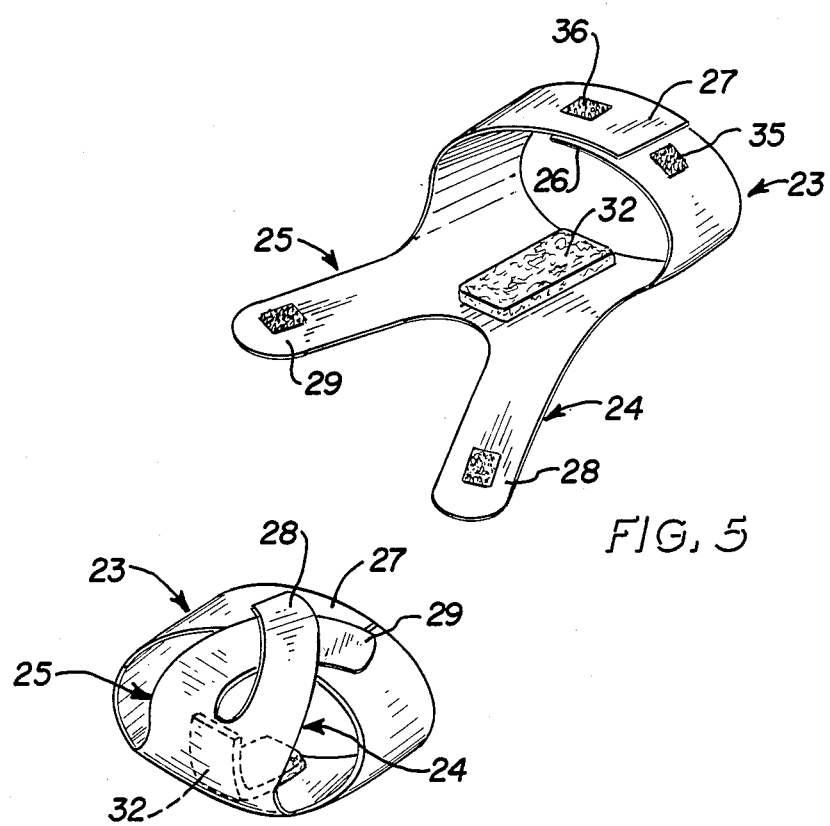
FIG. 5
FIG. 6

DOG DIAPER

This invention relates to a diaper for dogs and other small animals. It is more particularly concerned with a diaper adapted to be held in place on the animal by means which fasten at the animal's back. While my invention to be described hereinafter is particularly adapted to dogs it is suitable for any small quadruped kept as a pet.

BACKGROUND OF THE INVENTION

Many diaper-like devices have been designed for dogs and other small quadrupeds. Some of these resemble diapers for human infants in that they are unitary, encircle the dog's body and fasten at its belly. In that respect they are inconvenient to use as animals often resent being turned over on their backs. Others comprise a harness of some sort and an absorbent pad or receptacle detachable therefrom. The harness in some embodiments extends around the dog's legs. Again the fastening means to hold the harness in place and to attach the pad or receptacle thereto are on the dog's flanks or belly and are likewise inconvenient to use. Other devices comprise trousers of a sort, sometimes with elastic waist band and leg bands, in which the dog must be dressed, which operation may present difficulties.

SUMMARY OF THE INVENTION

My invention in its first preferred form comprises a textile body band which encircles the dog's body, a textile tail band extending at right angles from the body band at its mid point, an absorbent pad attached to the inner surface of the body band and the tail band at their junction and fastening means attached to each end of the body band and the free end of the tail band. The tail band has an opening intermediate its ends large enough for the dog's tail. To diaper a dog the tail band is passed between the dog's rear legs, and carried over the dog's rump. The dog's tail is passed through the opening in the tail band. The body band is slipped beneath the dog's body and its two ends are fastened together by their fasteners at the dog's back. The tail band is fastened to the ends of the body band, also at the dog's back.

BRIEF DESCRIPTION OF DRAWINGS

FIG. 4 is a plan view of a second preferred embodiment of my invention showing its inside surface.

FIG. 5 is a perspective view of the article of FIG. 4 with its body band ends connected to each other.

FIG. 6 is a perspective view of the article of FIG. 5 with its tail band connected to its body band.

DESCRIPTION OF PREFERRED EMBODIMENTS

Figure 1:
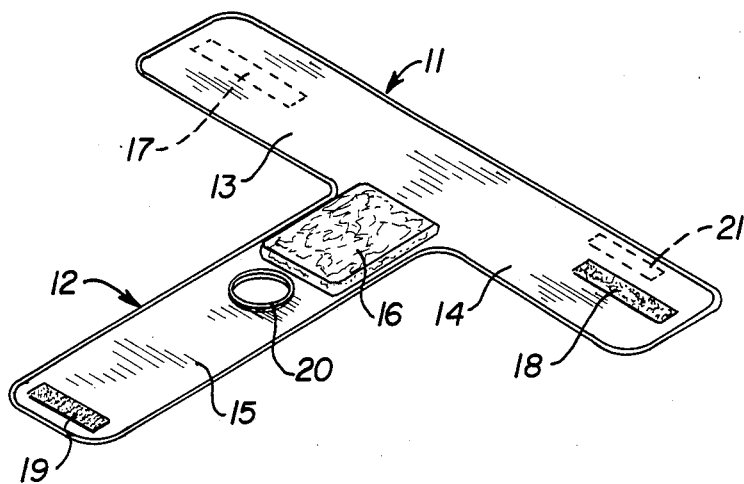
FIG. 1 is a plan view of a first preferred embodiment of my invention showing its inside surface.
Figure 2:
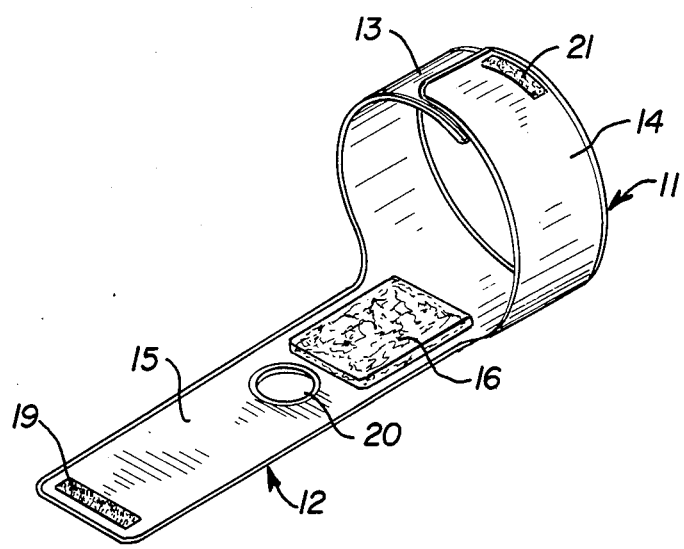
FIG. 2 is a perspective view of the article of FIG. 1 with its body band ends connected to each other.

A first preferred embodiment of my invention is shown in FIGS. 1–3 and 7. It comprises a body band 11 and tail band 12 each made of textile fabric, the tail band projecting from the body band at right angles thereto midway between ends 13 and 14 of body band 11. A pad 16 of absorbent flexible material is affixed to bands 11 and 12 at their junction as shown in FIG. 1. It is preferably detachable from bands 11 and 12 and held in place by a pressure-sensitive adhesive patch, not shown. On the outside surface of end 13 is affixed a patch 17 of a pile hook and loop connector, such as "Velcro", and on the inside surface of end 14 is affixed a mating patch 18 of the same fastener. On the inside surface of the free end 15 of tail band 12 is affixed a patch 19 of "Velcro" or the like. Tail band 12 is provided with an opening 20 intermediate its free end 15 and body band 11 of a size to allow a dog's tail to pass through. A drawstring 22 is attached to tail band 12 around opening 20. On the outside surface of body band 11 at end 14 is affixed a patch 21 of "Velcro" or the like as can be seen in FIG. 2.

Figure 3:
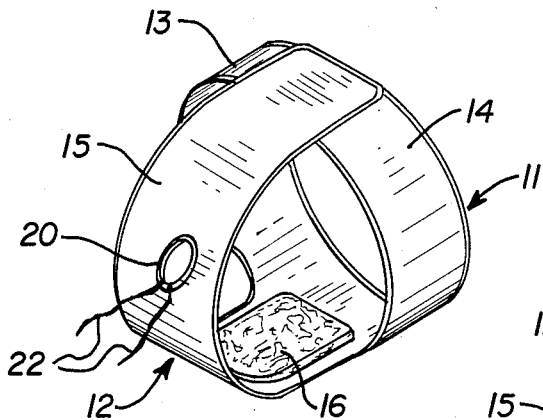
FIG. 3 is a perspective view of the article of FIG. 2 with its tail band connected to its body band ends.
Figure 7:
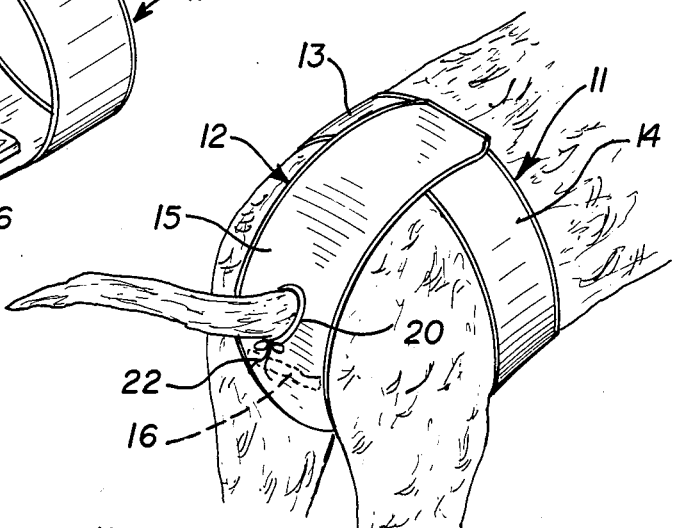
FIG. 7 is a fragmentary perspective of the rump of a dog wearing the article of FIGS. 1–3 inclusive.

That figure shows ends 13 and 14 of body band 11 connected as they would be with the body band at the back of the dog as shown in FIG. 7. The connection is made by mating patch 18 with patch 17, not visible in FIG. 2. FIG. 3 shows tail band end 15 connected with body bands 13 and 14 as it would be if brought between the hind legs of a dog and carried over his rump, shown in FIG. 7. That connection is made by meshing patch 19 with patch 21. FIG. 7 mentioned above shows my diaper in place with the dog's tail projecting through opening 20. The ends of drawstring 22 may be pulled together to contract opening 20 around the tail. As shown in FIG. 7 absorbent pad 16 is positioned against the dog's genital and anal areas and the connections between ends 13 and 14 of the body band 11 and end 15 of tail band 12 are all made on the back of the dog where they are readily accessible.

A second preferred embodiment of my diaper is shown in FIGS. 4, 5 and 6. It comprises a body band 23 and a bifurcated tail band comprising leg bands 24 and 25, each made of textile material, the leg bands projecting from body band 23 at its center and diverging from each other. A pad 32 of absorbent textile material is affixed to the inside surface of body band 23 and the common stem of leg bands 24 and 25 as shown in FIG. 4. It is preferably detachable from bands 23, 24 and 25 and is held in place by a pressure sensitive adhesive patch, now shown. On the inside surface of end 27 of body band 23 is affixed a patch 33 of a "Velcro" connector, and on the outside surface of end 26 is affixed a mating patch of mating "Velcro". On the inside ends 28 and 29 of leg bands 24 and 25 are affixed like patches 30 and 31 of "Velcro". On the outside surface of ends 26 and 27 are fixed "Velcro" patches 35 and 36 which mate with patches 31 and 30 respectively.

FIG. 5 shows ends 26 and 27 attached to each other as they would be with body band 23 in place at the back of the dog. The attachment is made by the "Velcro" patches above mentioned.

FIG. 6 shows leg bands 24 and 25 attached to body band ends 26 and 27 by their "Velcro" patches as they would be if brought between the hind legs of a dog and across his rump. The band ends 26 and 27 are crossed as shown so that diverging leg bands 24 and 25 come together around the tail of the dog. Absorbent pad 32 is positioned against the dog's genital and anal areas and the attachments between leg band ends and body band ends are all made on the back of the dog where they are readily accessible.

In the foregoing specification I have described presently preferred embodiments of my invention; however, it will be understood that my invention may be otherwise embodied within the scope of the following claims.

I claim:

1. A diaper for a small quadruped comprising a textile body band adapted to encircle the body of said quadruped, a textile tail band having one end attached to and extending from said body band midway of its ends and having a bifurcated free end at the other end, said tail band being adapted to pass from the belly between the rear legs of said quadruped and over its rump, a pad of absorbent material affixed to the inside surface of said body band and said tail band, an opening in said tail band intermediate said pad and the free end of said tail band formed by the bifurcated portions of said free end passing on each side and surrounding the tail of said quadruped in a closely adjacent relationship therewith, said bifurcated portions overlapping each other on the back of said quadruped, and fasteners attached to said body band and said tail band at their ends adapted to join said bands on said back of said quadruped and hold said bands around its body and rump, said pad of absorbent material being positioned against the genitals and anus of said quadruped by said bands.

2. The diaper of claim 1 in which said fasteners are pile hook-and-loop fasteners.

* * * * *